(12) United States Patent
Sadler et al.

(10) Patent No.: US 8,373,014 B2
(45) Date of Patent: *Feb. 12, 2013

(54) SOLID CATALYST HYDROCARBON ALKYLATION USING STACKED MOVING BED RADIAL FLOW REACTORS

(75) Inventors: Clayton C. Sadler, Arlington Heights, IL (US); Mary Jo Wier, Schaumburg, IL (US); Laurence O. Stine, Western Springs, IL (US); Christopher Naunheimer, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 253 days.

This patent is subject to a terminal disclaimer.

(21) Appl. No.: 12/958,737

(22) Filed: Dec. 2, 2010

(65) Prior Publication Data

US 2011/0152590 A1     Jun. 23, 2011

Related U.S. Application Data

(60) Provisional application No. 61/287,283, filed on Dec. 17, 2009.

(51) Int. Cl.
*C07C 2/58* (2006.01)

(52) U.S. Cl. ........ 585/716; 422/142; 422/145; 422/146; 585/446; 585/449; 585/709

(58) Field of Classification Search .................. 585/716, 585/709, 449, 446; 422/142, 145, 146
See application file for complete search history.

(56) References Cited

U.S. PATENT DOCUMENTS

| | | | | |
|---|---|---|---|---|
| 3,838,038 A | | 9/1974 | Greenwood et al. | |
| 3,839,197 A | * | 10/1974 | Greenwood et al. | 208/174 |
| 3,854,887 A | * | 12/1974 | Heinze et al. | 422/216 |
| 3,864,240 A | * | 2/1975 | Stone | 208/64 |
| 3,882,015 A | | 5/1975 | Carson | |
| 4,119,527 A | * | 10/1978 | Peters | 208/64 |
| 4,478,793 A | | 10/1984 | Vickers | |
| 4,869,808 A | * | 9/1989 | Vora et al. | 208/138 |
| 5,523,503 A | * | 6/1996 | Funk et al. | 585/446 |
| 5,849,976 A | | 12/1998 | Gosling et al. | |
| 5,998,687 A | * | 12/1999 | Woodle et al. | 585/449 |
| 7,622,620 B2 | | 11/2009 | Peters et al. | |
| 7,803,326 B2 | | 9/2010 | Fecteau et al. | |

OTHER PUBLICATIONS

Joachim Werther, "Fluidized-Bed Reactors," Apr. 15, 2007, Wiley-VCH, Ullman's Encyclopedia of Industrial Chemistry, p. 335.*

* cited by examiner

*Primary Examiner* — In Suk Bullock
*Assistant Examiner* — Candace R Chouinard
(74) *Attorney, Agent, or Firm* — Maryann Maas

(57) ABSTRACT

Systems and processes for the alkylation of a hydrocarbon are provided that utilize a plurality of moving bed radial flow reactors. An olefin injection point can be provided prior to each reactor by providing a mixer that mixes olefin with a hydrocarbon feed, or with the effluent stream from an upstream reactor, to produce a reactor feed stream. Catalyst can be provided from the reaction zone of one reactor to the reaction zone of a downstream reactor through catalyst transfer pipes, and can be regenerated after passing through the reaction zones of the reactors. The moving bed radial flow reactors can be stacked in one or more reactor stacks.

13 Claims, 3 Drawing Sheets

SOLID CATALYST HYDROCARBON ALKYLATION USING STACKED MOVING BED RADIAL FLOW REACTORS

CROSS REFERENCE TO RELATED APPLICATION

This application claims the benefit of priority of U.S. Provisional Application 61/287,283, filed Dec. 17, 2009, the contents of which are hereby incorporated by reference in its entirety.

FIELD OF THE INVENTION

The systems and processes described herein relate to hydrocarbon conversion, and particularly to alkylation of a hydrocarbon utilizing a solid catalyst. The systems and processes described herein can be utilized, for example, for alkylation of hydrocarbons such as aromatics or paraffins to produce useful chemicals and motor fuel.

DESCRIPTION OF RELATED ART

Alkylation is the reaction between a feed hydrocarbon and an alkylating agent. Hydrocarbon alkylation is widely used in the petroleum refining and petrochemical industries to produce a variety of useful acyclic and cyclic hydrocarbon products used as motor fuel, plastic and detergent precursors and petrochemical feedstocks.

In the production of motor fuels, the feed hydrocarbon is typically isobutane (I) and the alkylating agent is typically olefin (O). It is preferred to operate with an excess of isobutane in compared to olefin in order to promote the preferred alkylation reaction (I+O=Alkylate) instead of the undesirable oligomerization reaction (O+O=oligomer).

For example, large amounts of high octane gasoline are produced commercially by alkylation of isobutane with butenes or propylene. This significantly increases the value of the C4 feed hydrocarbons. Additionally, large amounts of valuable alkyl aromatic hydrocarbons including cumene, ethylbenzene and C10 to C15 linear alkylaromatics are produced by the alkylation of benzene with olefins of the appropriate carbon number.

Historically, liquid-acid alkylation processes have been used commercially, and such processes commonly employ hydrofluoric acid (HF) or sulfuric acid (H2SO4) as catalysts. Environmental and safety concerns, among other factors, have led to the development of alkylation processes utilizing solid catalysts. However, solid alkylation catalysts tend to have relatively quick deactivation times (e.g., about 2-24 hours) and require frequent regeneration.

Known liquid acid alkylating processes are typically designed with external isobutane to olefin ratios (I/O) between 5/1 and 15/1. External I/O is defined as total isobutane to the reaction section divided by the total feed olefin. It is desirable to have a solid catalyst alkylation process with the same range of external I/O ratios to remain cost competitive to liquid acid alkylation. The I/O ratio can be increased further inside the reactor section by recycling isobutane. This Internal I/O is defined as the local isobutane to local olefin concentration. The internal I/O ratio can also be increased by dividing the olefin feed into multiple injections, and requires mixing to ensure the feed olefin is completed dispersed in the reaction liquid stream. For solid catalyst alkylation, higher internal I/O ratios will result in longer catalyst lives and an improved product quality, but will also increase the capital and operating costs of the process.

It has been found that moving bed solid catalyst alkylation processes have a number of advantages over fixed bed solid catalyst alkylation processes, as described, for example, in U.S. Pat. No. 5,849,976 to Gosling, et al. at Col 2, lines 66-67 and Col 3, lines 1-9, which explains that the use of moving bed reactors has the advantage of reducing both the catalyst and liquid hydrocarbon inventory in the plant, which are desirable cost and safety benefits, and also that use of moving beds can function to transfer the catalyst between reaction and regeneration zones, which has the benefit of allowing the catalyst to be partially or totally replaced without disrupting the operation of the process. The U.S. Pat. No. 5,849,976 describes, for example, the utilization of slowly moving cylindrical beds of solid catalyst in a process featuring a cooling zone within the reaction zone and a moving bed catalyst regeneration zone. U.S. Pat. No. 5,849,976 at Abstract. Additionally, U.S. Pat. No. 3,838,038 to Greenwood et al. describes a method of operating a continuous hydrocarbon process employing solid catalyst particles that includes a moving bed reaction zone and a continuous regeneration zone. U.S. Pat. No. 3,838,038 at Col. 2 lines 25-30.

SUMMARY OF THE INVENTION

The systems and processes described herein relate to hydrocarbon alkylation using a solid catalyst in moving bed reactors.

In one aspect an alkylation process for the alkylation of a hydrocarbon is provided that includes the steps of: providing a plurality of moving bed reactors, the plurality of moving bed reactors including: a first moving bed reactor containing catalyst; and a second moving bed reactor containing catalyst; transferring catalyst from the first reaction zone of the first moving bed reactor to the second reaction zone of the second moving bed reactor; passing a hydrocarbon feed stream including an alkylation substrate and a first portion of an alkylating agent feed stream including an alkylating agent to a first mixer that produces a first reactor feed stream; providing the first reactor feed stream from the first mixer to the first reactor, wherein the first reactor feed stream contacts the catalyst and undergoes an alkylation reaction in the first reaction zone to produce a first reactor effluent stream, and first reactor effluent stream is removed from the first reactor through a first outlet; passing first reactor effluent stream and a second portion of the alkylating agent feed stream to a second mixer that produces a second reactor feed stream, the first reactor effluent stream having a pressure at the second mixer inlet that is lower than a pressure of the first reactor effluent stream when it is removed from the first outlet; and providing the second reactor feed stream from the second mixer to the second reactor, the second reactor feed stream having a pressure that is lower than the pressure of the first reactor effluent stream at the second mixer inlet, wherein the second reactor feed stream contacts catalyst and undergoes an alkylation reaction in the second reaction zone to produce a second reactor effluent stream, and second reactor effluent stream is removed from the second reactor through a second outlet.

More specifically, the systems and processes described herein relate to hydrocarbon alkylation using a solid catalyst in moving bed radial flow reactors.

In one aspect an alkylation process for the alkylation of a hydrocarbon is provided that includes the steps of: providing a plurality of moving bed radial flow reactors, transferring catalyst from the first reaction zone of the first moving bed radial flow reactor to the second reaction zone of the second moving bed radial flow reactor, passing a hydrocarbon feed stream and a first portion of an alkylating agent feed stream to a first mixer that produces a first reactor feed stream, providing the first reactor feed stream from the first mixer to the first reactor that produces a first reactor effluent stream, passing the first reactor effluent stream and a second portion of the alkylating agent feed stream to a second mixer that produces a second reactor feed stream, and providing the second reactor feed stream from the second mixer to the second reactor.

In a second aspect, an alkylation process for the alkylation of a hydrocarbon is provided that includes the steps of: providing a plurality of moving bed radial flow reactors configured in at least one vertical reactor stack having a top and a bottom, transferring catalyst from the first reaction zone of the first moving bed radial flow reactor to the second reaction zone of the second moving bed radial flow reactor through at least one catalyst transfer pipe, passing a hydrocarbon feed stream and a first portion of an alkylating agent feed stream to a first mixer that produces a first reactor feed stream, providing the first reactor feed stream from the first mixer to the first reactor that produces a first reactor effluent stream, passing the first reactor effluent stream and a second portion of the alkylating agent feed stream to a second mixer that produces a second reactor feed stream, and providing the second reactor feed stream from the second mixer to the second reactor.

In each aspect, the hydrocarbon feed stream can include an alkylation substrate, and the first portion of an alkylating agent feed stream can include an alkylating agent. Additionally, the plurality of moving bed radial flow reactors can include a first moving bed radial flow reactor including a first outer annulus, a first centerpipe having a first centerpipe outlet, and a first reaction zone containing catalyst; and a second moving bed radial flow reactor including a second outer annulus, a second centerpipe having a first centerpipe outlet, and a second reaction zone containing catalyst. The first reactor feed stream can be received by the first outer annulus of the first moving bed radial flow reactor, can flow radially inward through the first reaction zone towards the first centerpipe, and can undergo an alkylation reaction in the first reaction zone to produce a first reactor effluent stream. The first reactor effluent stream can be removed from the first reactor through the first centerpipe outlet. The pressure of the of the first reactor effluent stream at the second mixer inlet is lower than the first reactor effluent stream when it is removed from the first centerpipe. Additionally, the pressure of the second reactor feed stream is lower than the first reactor effluent stream at the second mixer inlet. The second reactor feed stream can be received by the second outer annulus, can flow radially inward through the second reaction zone towards the second centerpipe, and can undergo an alkylation reaction in the second reaction zone to produce a second reactor effluent stream. Finally, the second reactor effluent stream can be removed from the second reactor through the second centerpipe outlet.

BRIEF DESCRIPTION OF THE DRAWINGS

Specific examples have been chosen for purposes of illustration and description, and are shown in the accompanying drawings, forming a part of the specification.

DETAILED DESCRIPTION

Figure 1:
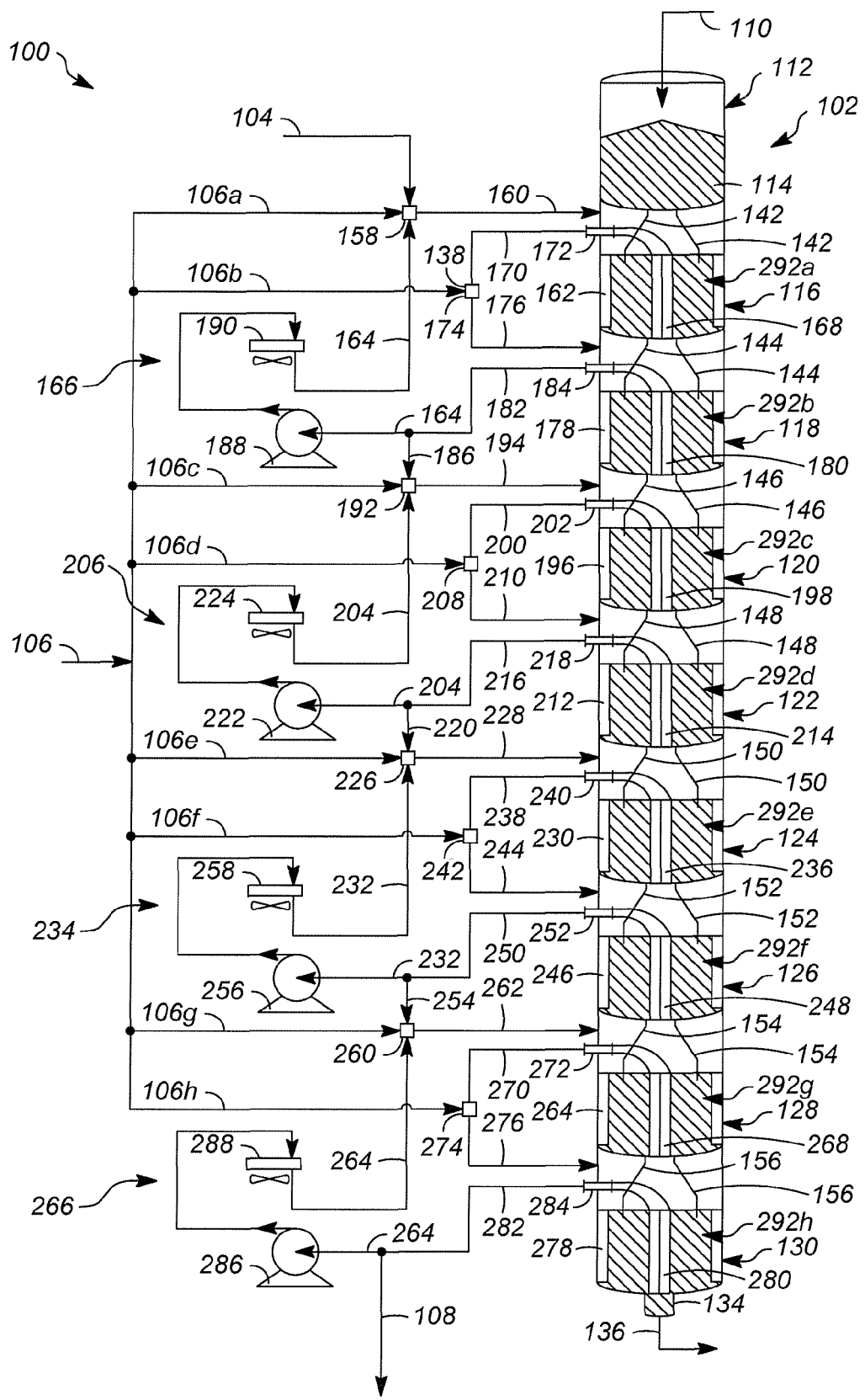
FIG. 1 illustrates one example of an alkylation system utilizing a single stack of reactors.

FIG. 1 illustrates one example of an alkylation system, illustrated generally at 100. Alkylation system 100 is a solid catalyst alkylation process, and can be utilized for the alkylation of a hydrocarbon. For example, alkylation system 100 can be utilized, to conduct isotbutane-olefin alkylation. In such an alkylation process, isobutene reacts with an acid site to form a tertiary carbenium ion ($tC_4^+$). The $tC_4^+$ ion reacts with an olefin molecule ($C_4=$) to form a larger tertiary carbenium ion ($tC_8^+$). The $tC_8^+$ ion undergoes hydride transfer with isobutane ($iC_4$), releasing an iso-octane (alkylate) molecule ($iC_8$) and reproducing the $tC_4^+$ ion.

Alkylation system 100 includes a plurality of moving bed radial flow reactors. Moving bed radial flow reactors are described herein, however, moving bed reactors may be employed instead of or in combination with moving bed radial flow reactors. Each moving bed radial flow reactor can include a reaction zone in which the alkylation reaction occurs. The alkylation reaction any of the plurality of moving bed radial flow reactors can have a reaction temperature from about 10° C. to about 100° C.

The plurality of moving bed radial flow reactors can include from about four moving bed radial flow reactors to about thirty moving bed radial flow reactors. In one example, the plurality of moving bed radial flow reactors can be configured in at least one vertical reactor stack having a top and a bottom. In a second example, the plurality of moving bed radial flow reactors can be configured in at least a first vertical reactor stack and a second vertical reactor stack. The plurality of moving bed radial flow reactors can be configured in more than two vertical reactor stacks.

Figure 3:
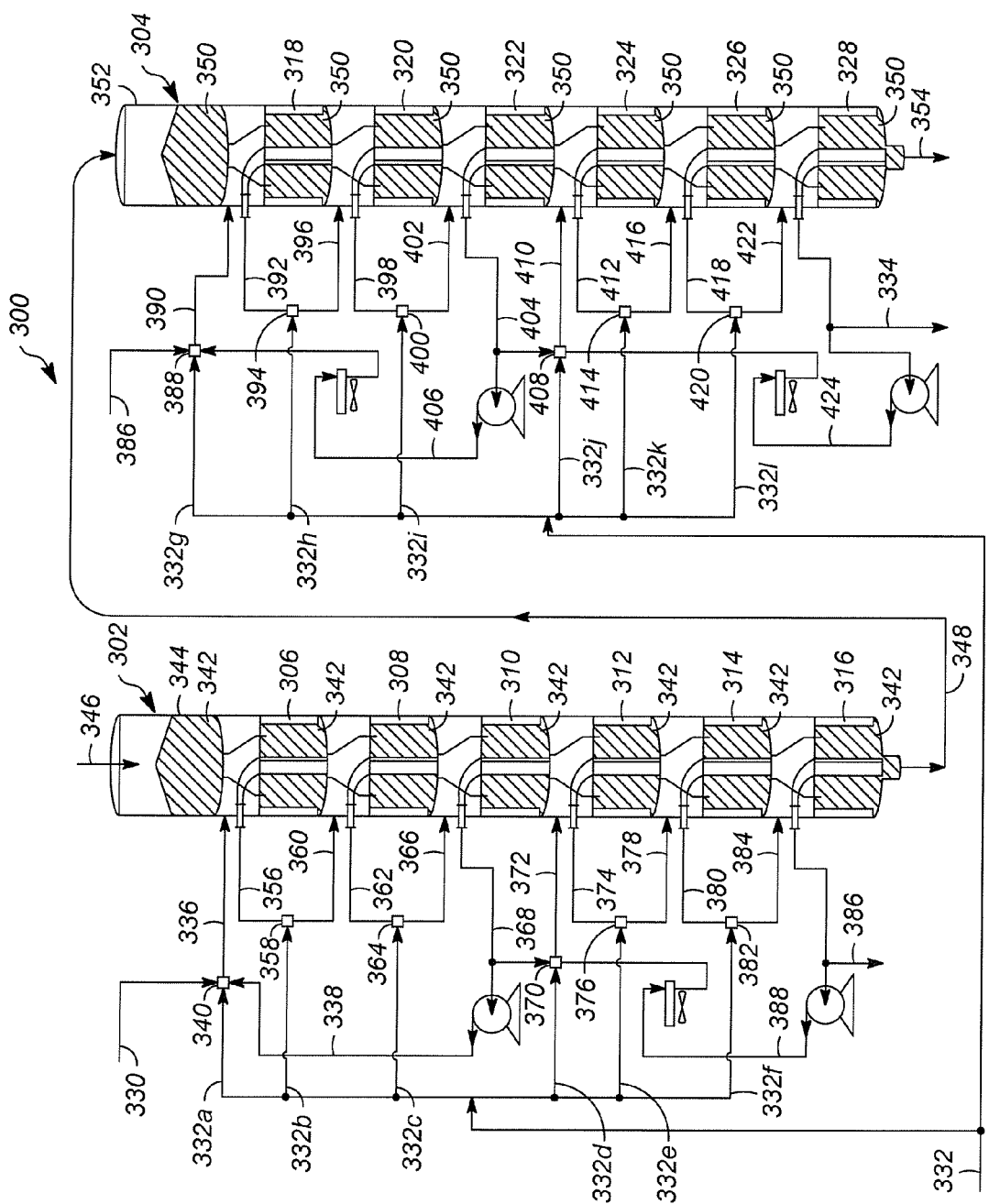
FIG. 3 illustrates one example of an alkylation system utilizing a double stack of reactors.

Some examples of alkylation systems and processes described herein can include one reactor stack, or a plurality of reactor stacks. In one example, a vertical reactor stack can include at least the four moving bed radial flow reactors. As illustrated in FIG. 1, vertical reactor stack 102 has eight moving bed radial flow reactors, including first moving bed radial flow reactor 116, second moving bed radial flow reactor 118, third moving bed radial flow reactor 120, fourth moving bed radial flow reactor 122, fifth moving bed radial flow reactor 124, sixth moving bed radial flow reactor 126, seventh moving bed radial flow reactor 128, and eighth moving bed radial flow reactor 130. As illustrated in FIG. 3, alkylation system 300 includes a first vertical reactor stack 302 and a second vertical reactor stack 304. First vertical reactor stack 302 has six moving bed radial flow reactors, including first moving bed radial flow reactor 306, second moving bed radial flow reactor 308, third moving bed radial flow reactor 310, fourth moving bed radial flow reactor 312, fifth moving bed radial flow reactor 314, and sixth moving bed radial flow reactor 316. Second vertical reactor stack 304 also has six moving bed radial flow reactors, including first moving bed radial flow reactor 318, second moving bed radial flow reactor 320, third moving bed radial flow reactor 322, fourth moving bed radial flow reactor 324, fifth moving bed radial flow reactor 326, and sixth moving bed radial flow reactor 328. In an alkylation system having two or more vertical reactor stacks, the vertical reactor stacks can have the same number of moving bed radial flow reactors, or different numbers of moving bed radial flow reactors.

The number of radial flow reactors to be used in an alkylation system can be determined by evaluating the benefit of an additional olefin injection point and the corresponding decrease in circulating liquid against the costs associated with adding an additional reactor. As reactors are added to a reactor stack, the stack increases in height, and it is preferred that reactor stacks be limited in height for practical considerations. Accordingly, it is preferred that two or more reactor stacks be utilized for alkylation systems that include more than eight reactors. Although, it is recognized that two or more reactor stacks can be utilized for alkylation systems that include eight reactors or less, and that it can be possible to utilize one reactor stack alkylation systems that include more than eight reactors.

Referring back to FIGS. 1 and 2, a hydrocarbon feed stream 104 and an alkylating agent feed stream 106 can be provided through lines to the reactor stack 102 to produce an alkylate effluent product stream 108. The alkylate effluent product stream 108 can be in a liquid phase. The hydrocarbon feed stream can include an alkylation substrate, such as, for example, $C_3$-$C_5$ isoparaffins. The alkylating agent feed stream can include an alkylating agent, such as, for example, $C_3$-$C_5$ olefins. The alkylating agent feed stream is preferably divided into portions, and an alkylating agent injection point is preferably provided for each moving bed radial flow reactor in the reactor stack 102. The alkylation substrate and the alkylating agent can be provided to any of the moving bed radial flow reactors in a reactor feed stream, and the reactor feed stream can have a ratio of alkylation substrate to alkylating agent of from about 5:1 to about 15:1. The reactor feed streams can be in a liquid phase.

To promote the desired alkylation reaction, a catalyst stream 110 containing catalyst 114 can be provided the reaction zone of each moving bed radial flow reactor. Catalyst 114 can contain regenerated catalyst, fresh catalyst, or a combination of regenerated catalyst and fresh catalyst. As illustrated in FIG. 1, the vertical reactor stack 102 also includes a catalyst surge vessel 112 at the top of the vertical reactor stack 102 above the first moving bed radial flow reactor 116, and catalyst 114 can be provided to the catalyst surge vessel 112. Catalyst surge vessel 112 can then provide catalyst 114 to the reactors in the reactor stack 102.

The catalyst 114 can be transferred to each reactor of the reactor stack 102 via gravity. As catalyst 114 is provided to the catalyst surge vessel 112 in catalyst stream 110. The catalyst surge vessel can provide catalyst 114 to the first moving bed radial flow reactor 116 through at least one catalyst transfer pipe 142. As illustrated in FIG. 1, catalyst 114 can flow downwardly from the catalyst surge vessel 112 to the first reactor 116 through two catalyst transfer pipes 142.

Figure 2:
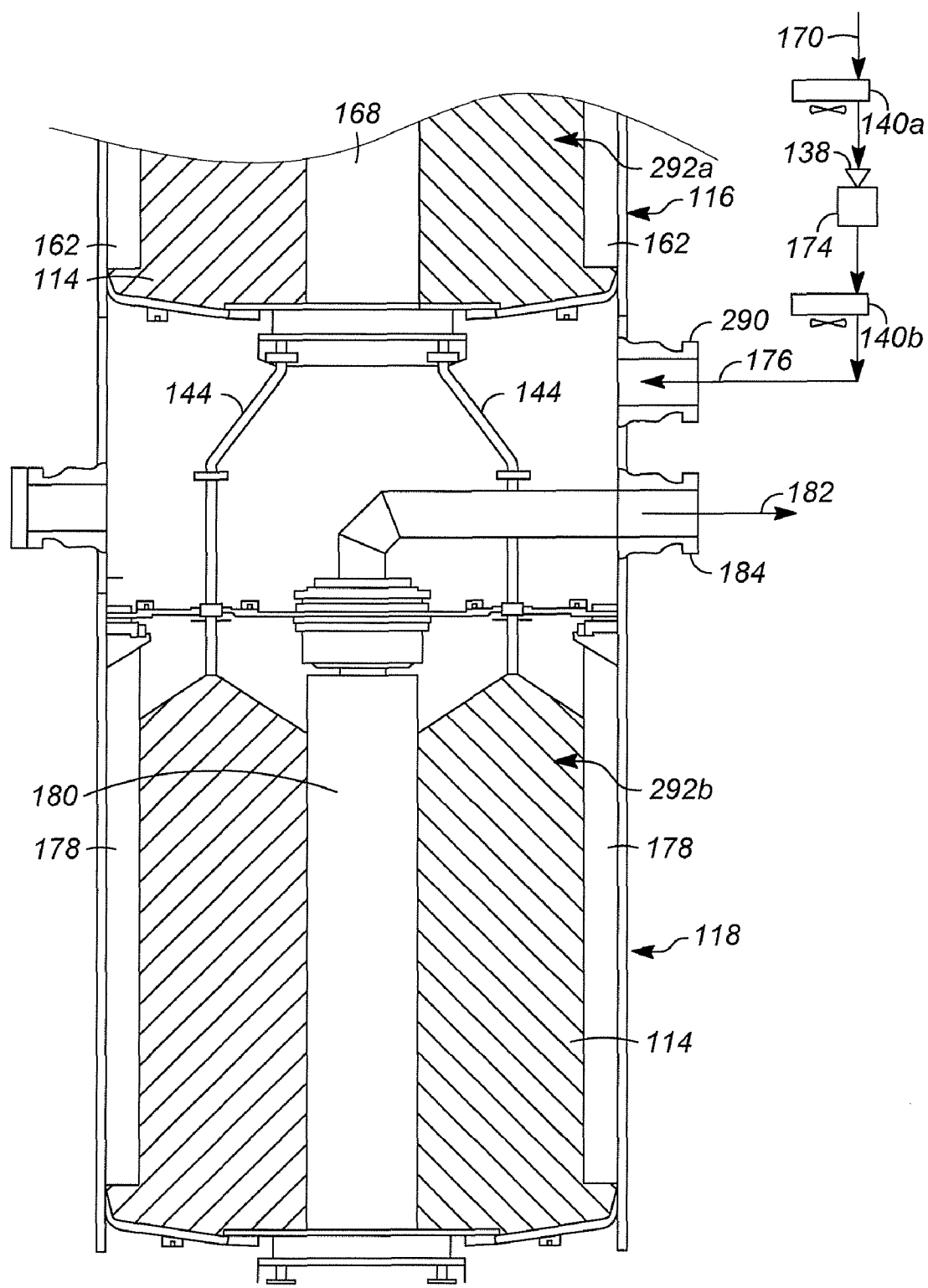
FIG. 2 illustrates a detail view of one reactor in the reactor stack of FIG. 1.

Referring to FIGS. 1 and 2, catalyst 114 can flow downwardly through the first reactor 116 via gravity, and can flow into the second reactor 118. For example, catalyst from the first reaction zone of the first moving bed radial flow reactor 116 can be transferred to the second reaction zone of the second moving bed radial flow reactor 118 through at least one catalyst transfer pipe 144. As illustrated in FIGS. 1 and 2, catalyst 114 can flow downwardly from the first reactor 116 to the second reactor 118 through two catalyst transfer pipes 144.

In the example illustrated in FIG. 1, there are at least two catalyst transfer pipes that transfer catalyst from each reactor to each subsequent reactor. In an alternative example, a single catalyst transfer pipe can be used to transfer catalyst from any one reactor to another reactor. The catalyst transfer pipes can be any suitable size. For example, catalyst transfer pipes can be sized to provide sufficient pressure drop for the mixers described below, while bypassing less than about 5% of the total reactor flow across the catalyst pipes.

As illustrated in FIGS. 1 and 2, catalyst 114 can be received by the second reactor 118 from the catalyst transfer pipes 144, and can flow downwardly through the second reactor 118 via gravity. Catalyst 114 can flow into the third reactor 120 via catalyst transfer pipes 146. Catalyst 114 can flow downwardly through the third reactor 120 via gravity, and can flow into the fourth reactor 122 through catalyst transfer pipes 148. Catalyst 114 can flow downwardly through the fourth reactor 122 via gravity, and can flow into the fifth reactor 124 through catalyst transfer pipes 150. Catalyst 114 can flow downwardly through the fifth reactor 124 via gravity, and can flow into the sixth reactor 126 through catalyst transfer pipes 152. Catalyst 114 can flow downwardly through the sixth reactor 126 via gravity, and can flow into the seventh reactor 128 through catalyst transfer pipes 154. Catalyst 114 can flow downwardly through the seventh reactor 128 via gravity, and can flow into the eighth reactor 130 through catalyst transfer pipes 156. In this manner, catalyst 114 flows via gravity through each reactor in the reactor stack 102.

Catalyst particles flow through the first reactor as a dense phase annular moving bed. At the outlet of first reactor, catalyst particles flow through catalyst transfer pipes before entering the second reactor. An aspect of the invention is the design of the catalyst transfer pipes. The catalyst transfer pipes are designed to transport the required flow of catalyst particles while minimizing the flow of process fluid. Process fluid that flows through the catalyst transfer pipes passes directly from the outlet of the upstream reactor to the next downstream reactor and bypassing the intended path of the process liquid through the unit operations between the upstream and downstream reactors.

It has been discovered that a key parameter in the design of the catalyst transfer pipes is the downward velocity of the liquid in the catalyst transfer pipes relative to the downward velocity of the catalyst particles. Low relative liquid velocities result in insufficient catalyst particle flow capacity of the catalyst transfer pipes. Also, low relative liquid velocities require increasing the catalyst transfer pipe length in order to develop the required liquid hydraulic resistance across the catalyst transfer pipe to balance the liquid hydraulic resistance through the unit operations between adjacent reactors.

High relative liquid velocities result in elevated liquid flow rates through the catalyst transfer pipes, which bypass the intended path of process liquid through the unit operations between adjacent reactors. High relative liquid velocities can also result in fluidization of the catalyst particles. Fluidization of the catalyst particles is very undesirable since it will likely lead to the breakage of catalyst particles. Fluidization of catalyst particles in the catalyst transfer pipes also dramatically reduces the liquid hydraulic resistance in the catalyst transfer pipes resulting in significantly higher liquid flow rates passing through the catalyst transfer pipes.

It has been found the range of relative liquid velocities in catalyst transfer pipes is typically required to be between 2 and 64 cm/s (0.07 and 2.1 feet per second) and the preferred range is between 3 and 79 cm/s (0.11 and 1.6 feet per second). In another embodiment the range of relative liquid velocities in catalyst transfer pipes may be between 1.5 and 123 cm/s (0.05 and 4.0 feet per second) and the preferred range between 3 and 76 cm/s (0.1 and 2.5 feet per second).

In each reactor in reactor stack 102, the catalyst can be utilized to react at least a portion of the hydrocarbon feed stream and at least a portion of the alkylating agent feed stream to produce alkylate effluent. As catalyst 114 is utilized in each of the reactors in the reactor stack 102, it can become deactivated. Deactivated catalyst can be removed from the bottom of the vertical reactor stack 102 in a deactivated catalyst stream 136 via an outlet 134, and a deactivated catalyst stream 136 can be provided to a catalyst regenerator (not shown), which can be a continuous catalyst regenerator, and the deactivated catalyst can be regenerated to produce regenerated catalyst. The regenerated catalyst can be provided back to top of the vertical reactor stack 102. As illustrated in FIG. 1, regenerated catalyst can be provided to the catalyst surge vessel 112 in catalyst stream 110.

Referring to FIG. 1, as described above, the alkylating agent feed stream 106 can be divided into one or more portions, such as first alkylating agent feed stream portion 106a, second alkylating agent feed stream portion 106b, third alkylating feed stream portion 106c, fourth alkylating agent feed stream portion 106d, fifth alkylating agent feed stream portion 106e, sixth alkylating agent feed stream portion 106f, seventh alkylating agent feed stream portion 106g, and eighth alkylating agent feed stream portion 106h.

The hydrocarbon feed stream 104 for the alkylation reaction can be provided to a first mixer 158, where it can be combined with first alkylating agent feed stream portion 106a. As illustrated, the mixers are external to the moving bed radial flow reactors. It should be understood, however, that the mixers described herein could alternatively be internal to the moving bed radial flow reactors. First reactor feed stream 160 can be provided from the first mixer 158, and can be injected into an outer annulus 162 of the first reactor 116. First reactor feed stream 160 can be in a liquid phase, and can contain the hydrocarbon feed stream 104 and the first alkylating agent feed stream portion 106a. First reactor feed stream 160 can also contain a circulation stream 164 of the reactor effluent from the second reactor 118, which can be provided to the first mixer 158 by first circulation loop 166. In an alternative embodiment, a circulation stream can be separated from a reactor effluent stream from another moving bed radial flow reactor downstream of the second moving bed radial flow reactor, and can be provided to the first mixer.

The first moving bed radial flow reactor 116 can include a first outer annulus 162, a first centerpipe 168 having a first centerpipe outlet 172, and a first reaction zone 292a containing catalyst. First reactor feed stream 160 can flow radially inward from the outer annulus 162 of the first reactor 116 towards the first centerpipe 168 of the first reactor 116. As the first reactor feed stream 160 flows radially inward through the first reactor 116, it passes through catalyst 114 in the first reaction zone 292a and can undergo alkylation to produce a first reactor effluent stream 170 that can be removed from the first reactor 116 via a first centerpipe outlet 172. First reactor effluent stream 170 can be in a liquid phase.

First reactor effluent stream 170 can be provided to second mixer 174 through the second mixer inlet 138, where it can be mixed with second alkylating agent feed stream portion 106b to form second reactor feed stream 176. The first reactor effluent stream 170 can have a pressure at the second mixer inlet 138 that is lower than a pressure of the first reactor effluent stream 170 when it is removed from the first reactor 116 through the first centerpipe outlet 172. Additionally, the second reactor feed stream 176 can have a pressure that is lower than the pressure of the first reactor effluent stream 172 at the second mixer inlet 138. The pressures of each subsequent reactor effluent stream and reactor feed stream can be designed in a similar manner. Such design of the pressures can facilitate flow of the of the reactor effluent streams and the reactor feed streams within the alkylation system 100 without requiring a pump or raise in pressure to provide a reactor effluent stream to a mixer, and then provide a reactor feed stream from a mixer to the next reactor. A system design that does not require pumping of the reactor effluent streams or reactor feed streams can provide a reduction in the capital and operation costs associated with adding olefin injection points and increasing the internal i/o ratio of the reactors.

As illustrated in FIG. 2, the alkylation system can include cooling a reactor effluent stream or a reactor feed stream to remove heat generated during the exothermic alkylation reaction. For example, the alkylation system can include cooling the first reactor effluent stream 170 or second reactor feed stream 176 in a cooling exchanger. In one example, the first reactor effluent stream 170 can be passed to a cooling exchanger 140a, to be cooled prior to being passed to the inlet 138 of the second mixer 174. In another example, second reactor feed stream 176 can be passed from the second mixer 174 to a cooling exchanger 140b. In an alkylation system where the pressure of the first reactor effluent is lower at the second mixer inlet 138 that at the first centerpipe outlet 172, and the pressure of the second reactor feed stream 176 is lower than the pressure of the first reactor effluent stream 170 at the second mixer inlet 138, the step of cooling the first reactor effluent stream 170 or the second reactor feed stream 176 can be accomplished without requiring a raise in pressure or pumping.

Referring to FIGS. 1 and 2, the second moving bed radial flow reactor 118 can include a second outer annulus 178, a second centerpipe 180 having a second centerpipe outlet 184, and a second reaction zone 292b containing catalyst. Second reactor feed stream 176 can be injected through a second reactor inlet 290 into the outer annulus 178 of the second reactor 118. As the second reactor feed stream 176 flows radially inward through the second reactor 118 to the second reactor centerpipe 180, it passes through catalyst 114 in the second reaction zone 292b and can undergo alkylation to produce a second reactor effluent stream 182, which can be in a liquid phase, and can be removed from the second reactor 118 via a second centerpipe outlet 184.

As illustrated in FIG. 1, second reactor effluent stream 182 can be divided into at least two portions, including circulation stream 164 and reaction portion 186. Circulation stream 164 can be separated from the second reactor effluent stream 182, and can be provided to the first mixer through the first circulation loop 166. First circulation loop 166 can include at least one pump 188. First circulation loop 166 can also include at least one cooling exchanger 190, which can cool the circulation stream 164 prior to providing the circulation stream to the first mixer in order to remove heat generated during the alkylation reaction. Reaction portion 186 of the second reactor effluent stream 182 can be provided to third mixer 192, where it can be combined with third alkylating agent feed stream portion 106c.

The third moving bed radial flow reactor 120 can include a third outer annulus 196, a third centerpipe 198 having a third centerpipe outlet 202, and a third reaction zone 292c containing catalyst. The third reactor feed stream 194 can be provided from the third mixer 192, and can be injected into an outer annulus 196 of the third reactor 120. Third reactor feed stream 194 can contain the reaction portion 186 of second reactor effluent stream 182 and third alkylating agent feed stream portion 106c. Third reactor feed stream 194 can also contain a circulation stream 204 of the alkylate effluent from the fourth reactor 122, which can be provided to the third mixer 192 by second circulation loop 206.

Third reactor feed stream 194 can flow radially inward from the outer annulus 196 of the third reactor 120 to the third centerpipe 198 of the third reactor 120. As the third reactor feed stream 194 flows radially inward through the third reactor 120, it passes through catalyst 114 in the third reaction zone 292c and can undergo alkylation to produce a third reactor effluent stream 120 that can be removed from the third reactor 120 via a third centerpipe outlet 202. Third reactor effluent stream 200, which can be in a liquid phase, can be provided to fourth mixer 208, where it can be mixed with fourth alkylating agent feed stream portion 106d to form fourth reactor feed stream 210.

The fourth moving bed radial flow reactor 122 can include a fourth outer annulus 212, a fourth centerpipe 214 having a fourth centerpipe outlet 218, and a fourth reaction zone 292*d* containing catalyst. Fourth reactor feed stream 210 can be injected into the outer annulus 212 of the fourth reactor 122. Fourth reactor feed stream 210 can flow radially inward from the outer annulus 212 of the fourth reactor 122 to the fourth centerpipe 214 of the fourth reactor 122. As the fourth reactor feed stream 210 flows radially inward through the fourth reactor 122, it passes through catalyst 114 in the fourth reaction zone 292*d* and can undergo alkylation to produce a fourth reactor effluent stream 216, which can be in a liquid phase, and can be removed from the fourth reactor 122 via a fourth centerpipe outlet 218.

Fourth reactor effluent stream 216 can be divided into at least two portions, including circulation stream 204 and reaction portion 220. Circulation stream 204 of the fourth reactor effluent stream 216 can be provided to second circulation loop 206. Second circulation loop 206 can include at least one pump 222. Second circulation loop 206 can also include at least one cooling exchanger 224, which can cool the circulation stream 204 of the fourth reactor effluent stream 216 to remove heat generated during the alkylation reaction to remove heat generated during the alkylation reaction. Reaction portion 220 of the fourth reactor effluent stream 216 can be provided to fifth mixer 226, where it can be combined with fifth alkylating agent feed stream portion 106*e*.

The fifth moving bed radial flow reactor 124 can include a fifth outer annulus 230, a fifth centerpipe 236 having a fifth centerpipe outlet 240, and a fifth reaction zone 292*e* containing catalyst. Fifth reactor feed stream 228 can be provided from the fifth mixer 226, and can be injected into an outer annulus 230 of the fifth reactor 124. Fifth reactor feed stream 228 can contain the reaction portion 220 of fourth reactor effluent stream 216 and fifth alkylating agent feed stream portion 106*e*. Fifth reactor feed stream 228 can also contain a circulation stream 232 of the alkylate effluent from the sixth reactor 126, which can be provided to the fifth mixer 226 by third circulation loop 234.

Fifth reactor feed stream 228 can flow radially inward from the outer annulus 230 of the fifth reactor 124 to the fifth centerpipe 236 of the fifth reactor 124. As the fifth reactor feed stream 228 flows radially inward through the fifth reactor 124, it passes through catalyst 114 in the fifth reaction zone 292*e* and can undergo alkylation to produce a fifth reactor effluent stream 238 that can be removed from the fifth reactor 124 via a fifth centerpipe outlet 240. Fifth reactor effluent stream 238, which can be in a liquid phase, can be provided to sixth mixer 242, where it can be mixed with sixth alkylating agent feed stream portion 106*f* to form sixth reactor feed stream 244.

The sixth moving bed radial flow reactor 126 can include a sixth outer annulus 246, a sixth centerpipe 248 having a sixth centerpipe outlet 252, and a sixth reaction zone 292*f* containing catalyst. Sixth reactor feed stream 244 can be injected into the outer annulus 246 of the sixth reactor 126. Sixth reactor feed stream 244 can flow radially inward from the outer annulus 246 of the sixth reactor 126 to the sixth centerpipe 248 of the sixth reactor 126. As the sixth reactor feed stream 244 flows radially inward through the sixth reactor 126, it passes through catalyst 114 in the sixth reaction zone 292*f* and can undergo alkylation to produce a sixth reactor effluent stream 250, which can be in a liquid phase, and can be removed from the sixth reactor 126 via a sixth centerpipe outlet 252.

Sixth reactor effluent stream 250 can be divided into at least two portions, including circulation stream 232 and reaction portion 254. Circulation stream 232 of the sixth reactor effluent stream 250 can be provided to third circulation loop 234. Third circulation loop 234 can include at least one pump 256. Third circulation loop 234 can also include at least one cooling exchanger 258, which can cool the circulation stream 232 of the sixth reactor effluent stream 250 to remove heat generated during the alkylation reaction. Reaction portion 254 of the sixth reactor effluent stream 250 can be provided to seventh mixer 260, where it can be combined with seventh alkylating agent feed stream portion 106*g*.

The seventh moving bed radial flow reactor 128 can include a seventh outer annulus 264, a seventh centerpipe 268 having a seventh centerpipe outlet 272, and a seventh reaction zone 292*g* containing catalyst. Seventh reactor feed stream 262 can be provided from the seventh mixer 260, and can be injected into an outer annulus 264 of the seventh reactor 128. Seventh reactor feed stream 262 can contain the reaction portion 254 of sixth reactor effluent stream 250 and seventh alkylating agent feed stream portion 106*g*. Seventh reactor feed stream 262 can also contain a circulation stream 264 of the alkylate effluent from the eighth reactor 130, which can be provided to the seventh mixer 260 by fourth circulation loop 266.

Seventh reactor feed stream 262 can flow radially inward from the outer annulus 264 of the seventh reactor 128 to the seventh centerpipe 266 of the seventh reactor 128. As the seventh reactor feed stream 262 flows radially inward through the seventh reactor 128, it passes through catalyst 114 in the seventh reaction zone 292*g* and can undergo alkylation to produce a seventh reactor effluent stream 270 that can be removed from the seventh reactor 128 via a seventh centerpipe outlet 272. Seventh reactor effluent stream 272, which can be in a liquid phase, can be provided to eighth mixer 274, where it can be mixed with eighth alkylating agent feed stream portion 106*h* to form eighth reactor feed stream 276.

The eighth moving bed radial flow reactor 130 can include a eighth outer annulus 278, a eighth centerpipe 280 having a eighth centerpipe outlet 284, and a eighth reaction zone 292*h* containing catalyst. Eighth reactor feed stream 276 can be injected into the outer annulus 278 of the eighth reactor 130. Eighth reactor feed stream 276 can flow radially inward from the outer annulus 278 of the eighth reactor 130 to the eighth centerpipe 280 of the eighth reactor 130. As the eighth reactor feed stream 276 flows radially inward through the eighth reactor 130, it passes through catalyst 114 in the eighth reaction zone 292*h* and can undergo alkylation to produce a eighth reactor effluent stream 282 that can be removed from the eighth reactor 130 via a eighth centerpipe outlet 284.

The eighth reactor effluent stream 282 can be divided. A recirculation stream 264 of the eighth reactor effluent stream 282 can be provided to the fourth circulation loop 266. Fourth circulation loop 266 can include at least one pump 286. Fourth circulation loop 266 can also include at least one cooling exchanger 288, which can cool the circulation stream 264 of the eighth reactor effluent stream 282 to remove heat generated during the alkylation reaction. The remaining portion of eighth reactor effluent stream 282 can be removed from the alkylation system 100 as alkylate effluent product stream 108. In at least one example, the alkylate effluent product stream 108 can be provided to a downstream unit, such as an isostripper, for further processing.

FIG. 3 illustrates an alkylation system 300 that includes a first vertical reactor stack 302 and a second vertical reactor stack 304. As discussed above, the first vertical reactor stack 302 and the second vertical reactor stack each include six moving bed radial flow reactors. The alkylation system 300 can function in a similar manner to alkylation system 100 with respect to the structure of the moving bed radial flow reactors, and the flow scheme of the reactor feed streams and reactor effluent streams.

A hydrocarbon feed stream 330 and an alkylating agent feed stream 332 can be provided through lines to the first reactor stack 302, and the alkylation system 300 can produce an alkylate effluent product stream 334. The alkylating agent feed stream is preferably divided into portions, and an alkylating agent injection point is preferably provided for each moving bed radial flow reactor in the first reactor stack 302 and the second reactor stack 304. As illustrated in FIG. 3, the alkylating agent feed stream is divided into twelve portions, 332a through 332l, and each portion of the alkylating agent feed stream is provided to a mixer that provides a reactor feed stream to one of the moving bed radial flow reactors.

As illustrated in FIG. 3, the hydrocarbon feed stream 330 and the first alkylating agent feed stream portion 332a are provided to a first mixer 340. A circulation stream 338 can be separated from the reactor effluent stream of a reactor downstream of the first reactor 306, and can also be provided to the first mixer 340. first mixer 340 can provide a first reactor feed stream 336 to the first moving bed radial flow reactor 306.

Catalyst 342 can be provided to the first reactor 306 from a catalyst surge vessel 344 that receives a catalyst stream 346. The catalyst stream 346 can contain fresh catalyst, regenerated catalyst, or a combination of fresh and regenerated catalyst. The catalyst 342 can flow downward through a reaction zone in each reactor in the first vertical reactor stack 302, and can participate in the alkylation reaction occurring in each reaction zone. Catalyst can be removed from the first reactor stack 302 in a first reactor stack catalyst stream 348. Catalyst 350 from the first reactor stack catalyst stream 348 can be provided to a second catalyst surge vessel 352 at the top of the second vertical reactor stack 304. In one example, fresh or regenerated catalyst can also be provided to the second catalyst surge vessel 352, or at least a portion of the catalyst in the first reactor stack catalyst stream 348 can be regenerated prior to being provided to the second catalyst surge vessel 352. Catalyst 350 can flow downward through a reaction zone in each reactor in the second vertical reactor stack 304, and can participate in the alkylation reaction occurring in each reaction zone. A deactivated catalyst stream 354 can be removed from the bottom of the second vertical reactor stack 304.

The first reactor feed stream 336 can undergo an alkylation reaction in the reaction zone of the first moving bed radial flow reactor 306, and a first reactor effluent stream can be removed from the first moving bed radial flow reactor 306. The first reactor effluent stream and the second alkylating agent feed stream portion 332b can be provided to a second mixer 358 that provides a second reactor feed stream 360 to the second reactor 308.

The alkylation system 300, like the alkylation system 100 discussed above, can be designed so that the pressure of the first reactor effluent stream is lower at the second mixer inlet than the pressure when it is removed from the first reactor, and so that the pressure of the second reactor feed stream is lower than the pressure of the first reactor effluent stream at the second mixer inlet. The pressures of each subsequent reactor effluent stream and reactor feed stream can be similarly designed.

The second reactor feed stream 360 can undergo an alkylation reaction in the reaction zone of the second moving bed radial flow reactor 308, and a second reactor effluent stream 362 can be removed from the second moving bed radial flow reactor 308. The second reactor effluent stream and the third alkylating agent feed stream portion 332c can be provided to a third mixer 364 that provides a third reactor feed stream 366 to the second reactor 310.

The third reactor feed stream 366 can undergo an alkylation reaction in the reaction zone of the third moving bed radial flow reactor 310, and a third reactor effluent stream 368 can be removed from the third moving bed radial flow reactor 310. A circulation stream 338 can be separated from the third reactor effluent stream 368, and the remainder can be provided, along with the fourth alkylating agent feed stream portion 332d to a fourth mixer 370 that provides a fourth reactor feed stream 372 to the fourth reactor 312.

The fourth reactor feed stream 372 can undergo an alkylation reaction in the reaction zone of the fourth moving bed radial flow reactor 312, and a fourth reactor effluent stream 374 can be removed from the fourth moving bed radial flow reactor 312. The fourth reactor effluent stream and the fifth alkylating agent feed stream portion 332e can be provided to a fifth mixer 376 that provides a fifth reactor feed stream 378 to the fifth reactor 314.

The fifth reactor feed stream 378 can undergo an alkylation reaction in the reaction zone of the fifth moving bed radial flow reactor 314, and a fifth reactor effluent stream 380 can be removed from the fifth moving bed radial flow reactor 314. The fifth reactor effluent stream 380 and the sixth alkylating agent feed stream portion 332f can be provided to a sixth mixer 382 that provides a sixth reactor feed stream 384 to the sixth reactor 316, which is the bottom reactor in the first vertical reactor stack 302.

A sixth reactor effluent stream 386 can be removed from the sixth reactor 316. A circulation stream 388 can be separated from the sixth reactor effluent stream 386 and can be passed to an upstream mixer, such as fourth mixer 370, where it can be mixed into a reactor feed stream. At least a portion of the remainder of the sixth reactor effluent stream 386 can be passed to the top of the second vertical reactor stack 304 to undergo further alkylation.

As illustrated in FIG. 3, sixth reactor effluent stream 386 and seventh alkylating agent feed stream portion 332g can be provided to a seventh mixer 388 that provides a seventh reactor feed stream 390 to the first reactor 318 of the second vertical reactor stack 304.

The seventh reactor feed stream 390 can undergo an alkylation reaction in the reaction zone of the first moving bed radial flow reactor 318 of the second vertical reactor stack 304, and a seventh reactor effluent stream 392 can be removed from the first moving bed radial flow reactor 318 of the second vertical reactor stack 304. The seventh reactor effluent stream 392 and the eighth alkylating agent feed stream portion 332h can be provided to a eighth mixer 394 that provides a eighth reactor feed stream 396 to the second moving bed radial flow reactor 320 of the second vertical reactor stack 304.

The eighth reactor feed stream 396 can undergo an alkylation reaction in the reaction zone of the second moving bed radial flow reactor 320 of the second vertical reactor stack 304, and an eighth reactor effluent stream 398 can be removed from the second moving bed radial flow reactor 320 of the second vertical reactor stack 304. The eighth reactor effluent stream 398 and the ninth alkylating agent feed stream portion 332i can be provided to a ninth mixer 400 that provides a ninth reactor feed stream 402 to the third moving bed radial flow reactor 322 of the second vertical reactor stack 304.

The ninth reactor feed stream 403 can undergo an alkylation reaction in the reaction zone of the third moving bed radial flow reactor 322 of the second vertical reactor stack 304, and a ninth reactor effluent stream 404 can be removed from the third moving bed radial flow reactor 322 of the second vertical reactor stack 304. A circulation stream 406 can be separated from the ninth reactor effluent stream 404 and can be provided to an upstream mixer to be combined into a reactor feed stream. The remainder of the ninth reactor effluent stream 404 and the tenth alkylating agent feed stream portion 332j can be provided to a tenth mixer 408 that provides a tenth reactor feed stream 410 to the fourth moving bed radial flow reactor 324 of the second vertical reactor stack 304.

The tenth reactor feed stream 410 can undergo an alkylation reaction in the reaction zone of the fourth moving bed radial flow reactor 324 of the second vertical reactor stack 304, and a tenth reactor effluent stream 412 can be removed from the fourth moving bed radial flow reactor 324 of the second vertical reactor stack 304. The tenth reactor effluent stream 412 and the eleventh alkylating agent feed stream portion 332k can be provided to an eleventh mixer 414 that provides an eleventh reactor feed stream 416 to the fifth moving bed radial flow reactor 326 of the second vertical reactor stack 304.

The eleventh reactor feed stream 416 can undergo an alkylation reaction in the reaction zone of the fifth moving bed radial flow reactor 326 of the second vertical reactor stack 304, and an eleventh reactor effluent stream 418 can be removed from the fifth moving bed radial flow reactor 326 of the second vertical reactor stack 304. The eleventh reactor effluent stream 418 and the twelfth alkylating agent feed stream portion 332l can be provided to a twelfth mixer 420 that provides an twelfth reactor feed stream 422 to the sixth moving bed radial flow reactor 328, which is the bottom reactor of the of the second vertical reactor stack 304.

The twelfth reactor feed stream 422 can undergo an alkylation reaction in the reaction zone of the sixth moving bed radial flow reactor 328 of the second vertical reactor stack 304, and the alkylate effluent product stream 334 can be removed from the sixth moving bed radial flow reactor 328 of the second vertical reactor stack 304. A circulation stream 424 can be separated from the alkylate effluent product stream 334, and can be provided to an upstream mixer to be combined into a reactor feed stream.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

The invention claimed is:

1. An alkylation process for the alkylation of a hydrocarbon, the alkylation process comprising the steps of:
   providing a plurality of moving bed radial flow reactors, the plurality of moving bed radial flow a reactors including:
      a first moving bed radial flow reactor including a first outer annulus, a first centerpipe having a first centerpipe outlet, and a first reaction zone containing catalyst; and
      a second moving bed radial flow reactor including a second outer annulus, a second centerpipe having a second centerpipe outlet, and a second reaction zone containing catalyst;
   transferring catalyst from the first reaction zone of the first moving bed radial flow reactor to the second reaction zone of the second moving bed radial flow reactor through at least two catalyst transfer pipes;
   passing a hydrocarbon feed stream comprising an alkylation substrate and a first portion of an alkylating agent feed stream to a first mixer that produces a first reactor feed stream;
   passing the first reactor feed stream to the first outer annulus which flows radially inward through the first reaction zone towards the first centerpipe and undergoes an alkylation reaction to produce a first reactor effluent stream which is removed through the first centerpipe outlet;
   passing the first reactor effluent stream and a second portion of the alkylating agent feed stream to a second mixer that produces a second reactor feed stream, the first reactor effluent stream having a pressure at the second mixer inlet that is lower than a pressure of the first reactor effluent stream when it is removed from the first centerpipe; and
   passing the second reactor feed stream to the second reactor, the second reactor feed stream having a pressure that is lower than the pressure of the first reactor effluent stream at the second mixer inlet, wherein the second reactor feed stream is received by the second outer annulus and flows radially inward through the second reaction zone towards the second centerpipe and undergoes an alkylation reaction to produce a second reactor effluent stream which is removed from the second reactor through the second centerpipe outlet;
   wherein the reactor feed streams and the reactor effluent streams are in a liquid phase;
   wherein the second reactor effluent stream is divided into a circulation portion and a reaction portion;
   passing the circulation portion to the first mixer; and
   flowing the reaction portion to a third mixer without requiring a pump or raise in pressure and mixing with a third portion of an alkylating agent feed stream to produce a reactor feed stream to next reactor.

2. The alkylation process of claim 1, wherein the alkylation substrate in the hydrocarbon feed stream comprises $C3-C5$ isoparaffins, and the alkylating agent in the alkylating agent feed stream comprises $C3-C5$ olefins.

3. The alkylation process of claim 1, wherein the step of transferring catalyst comprises transferring catalyst from the first reaction zone of the first moving bed radial flow reactor to the second reaction zone of the second moving bed radial flow reactor through at least one catalyst transfer pipe.

4. The alkylation process of claim 1, wherein the plurality of moving bed radial flow reactors are configured in at least one vertical reactor stack having a top and a bottom, the vertical reactor stack comprising at least four moving bed radial flow reactors.

5. The alkylation process of claim 4, further comprising the steps of:
   removing catalyst from the bottom of the vertical reactor stack in a deactivated catalyst stream;
   regenerating the deactivated catalyst to produce regenerated catalyst; and
   providing the regenerated catalyst to the top of the vertical reactor stack.

6. The alkylation process of claim 5, the vertical reactor stack further comprising a catalyst surge vessel at the top of the vertical reactor stack above the first reactor, wherein the regenerated catalyst is provided to the catalyst surge vessel, and the catalyst surge vessel provides catalyst to the first moving bed radial flow reactor through at least one catalyst transfer pipe.

7. The alkylation process of claim 1, wherein the plurality of moving bed radial flow reactors comprises from about four moving bed radial flow reactors to about thirty moving bed radial flow reactors.

8. The alkylation process of claim 1, wherein the plurality of moving bed radial flow reactors are configured in at least a first vertical reactor stack and a second vertical reactor stack.

9. The alkylation process of claim 1, wherein the alkylation substrate and the alkylating agent are provided in the first reactor feed stream or the second reactor feed stream in a ratio of alkylation substrate to alkylating agent of from about 5:1 to about 15:1.

10. The alkylation process of claim 1, further comprising the step of cooling the first reactor effluent stream or second reactor feed stream in a cooling exchanger.

11. The alkylation process of claim 3, further comprising the step of:
cooling the circulation stream in a cooling exchanger prior to providing the circulation stream to the first mixer.

12. The alkylation process of claim 1, wherein the alkylation reaction in at least one of the moving bed radial flow reactors has a reaction temperature from about 10° C. to about 100° C.

13. The alkylation process of claim 1 wherein the catalyst is transferred from the first reaction zone of the first moving bed reactor to the second reaction zone of the second moving bed reactor through at least one catalyst transfer pipe while the catalyst is submerged in a liquid portion of the first reactor effluent stream; and
wherein the relative velocity of the liquid portion in the catalyst transfer pipe to the catalyst in the catalyst transfer pipe ranges from about 1.5 cm/s to about 123 cm/s (about 0.05 to about 4.0 feet per second).

\* \* \* \* \*